United States Patent
Petrucelli et al.

(10) Patent No.: US 10,820,828 B2
(45) Date of Patent: *Nov. 3, 2020

(54) PHYSICAL PARAMETER SENSING SYSTEM

(71) Applicant: Measurement Ltd., Grand Cayman (KY)

(72) Inventors: Steven Petrucelli, Cranbury, NJ (US); Jack Ko, Shenzhen (CN)

(73) Assignee: Measurement Ltd., Grand Cayman (KY)

( * ) Notice: Subject to any disclaimer, the term of this patent is extended or adjusted under 35 U.S.C. 154(b) by 142 days.

This patent is subject to a terminal disclaimer.

(21) Appl. No.: 16/265,445

(22) Filed: Feb. 1, 2019

(65) Prior Publication Data

US 2019/0159698 A1 May 30, 2019

Related U.S. Application Data

(63) Continuation of application No. 15/094,609, filed on Apr. 8, 2016, now Pat. No. 10,194,828.

(Continued)

(51) Int. Cl.
*A61B 5/00* (2006.01)
*A61B 5/053* (2006.01)
(Continued)

(52) U.S. Cl.
CPC ............ *A61B 5/0537* (2013.01); *A61B 5/002* (2013.01); *G06F 19/00* (2013.01);
(Continued)

(58) Field of Classification Search
CPC ..... A61B 5/002; G06F 19/3418; G06F 19/00; G16H 40/63
See application file for complete search history.

(56) References Cited

U.S. PATENT DOCUMENTS 8,521,942 B2  8/2013 Bhesania et al.
9,173,576 B2  11/2015 Yuen et al.
(Continued)

FOREIGN PATENT DOCUMENTS

KR   10-2014-0095610 A   8/2014

OTHER PUBLICATIONS

International Search Report for counterpart International Application No. PCT/US2016/026780 dated Jul. 19, 2016.

*Primary Examiner* — Aftab N. Khan
(74) *Attorney, Agent, or Firm* — Howard IP Law Group, PC

(57) ABSTRACT

A sensing apparatus for measuring at least one parameter includes at least one sensor for detecting at least one parameter and outputting a signal representative of the parameter. The sensing apparatus includes a memory for storing data and computer instructions and a communication component configured to transmit data representative of a value associated with the at least one parameter. A processor of the sensing apparatus communicates with the at least one sensor, the memory and the communication component. The processor receives output signals from said at least one sensor, and calculates at least one parameter based on computer instructions stored in the memory. The parameter is formatted in a human interface device (HID) compliant protocol, and provided to the communication component, which transmits the at least one HID compliant parameter value to a remote processing device.

20 Claims, 9 Drawing Sheets

Related U.S. Application Data

(60) Provisional application No. 62/145,911, filed on Apr. 10, 2015.

(51) Int. Cl.
  G06F 19/00 (2018.01)
  G16H 40/63 (2018.01)
  *G01G 19/50* (2006.01)
  *G01G 23/37* (2006.01)

(52) U.S. Cl.
  CPC ......... G06F 19/3418 (2013.01); G16H 40/63 (2018.01); *A61B 5/4872* (2013.01); *G01G 19/50* (2013.01); *G01G 23/3735* (2013.01)

(56) References Cited

U.S. PATENT DOCUMENTS

| | | | | |
|---|---|---|---|---|
| 9,655,053 | B2* | 5/2017 | Park | H04W 56/001 |
| 2005/0228691 | A1* | 10/2005 | Paparo | G06Q 50/22 |
| | | | | 705/2 |
| 2006/0094461 | A1* | 5/2006 | Hameed | G06F 3/038 |
| | | | | 455/552.1 |
| 2006/0290326 | A1* | 12/2006 | Bhesania | G05F 1/70 |
| | | | | 323/210 |
| 2008/0137578 | A1* | 6/2008 | Goldberg | H04N 1/00885 |
| | | | | 370/311 |
| 2012/0143663 | A1 | 6/2012 | Miller et al. | |
| 2013/0076533 | A1 | 3/2013 | Moran | |
| 2013/0289889 | A1 | 10/2013 | Yuen et al. | |
| 2014/0012512 | A1 | 1/2014 | Yuen et al. | |
| 2014/0182952 | A1 | 7/2014 | Yuen et al. | |
| 2014/0257053 | A1 | 9/2014 | Yuen et al. | |
| 2014/0257709 | A1 | 9/2014 | Yuen et al. | |
| 2014/0275852 | A1 | 9/2014 | Hong et al. | |
| 2014/0343443 | A1 | 11/2014 | Yuen et al. | |
| 2014/0377729 | A1 | 12/2014 | Yuen et al. | |
| 2015/0011845 | A1 | 1/2015 | Yuen et al. | |
| 2015/0067819 | A1* | 3/2015 | Shribman | H04L 67/32 |
| | | | | 726/12 |
| 2015/0293877 | A1* | 10/2015 | Liang | G06F 13/4068 |
| | | | | 710/33 |
| 2015/0377635 | A1 | 12/2015 | Beaurepaire et al. | |
| 2017/0014040 | A1* | 1/2017 | Shim | A61B 5/002 |

* cited by examiner

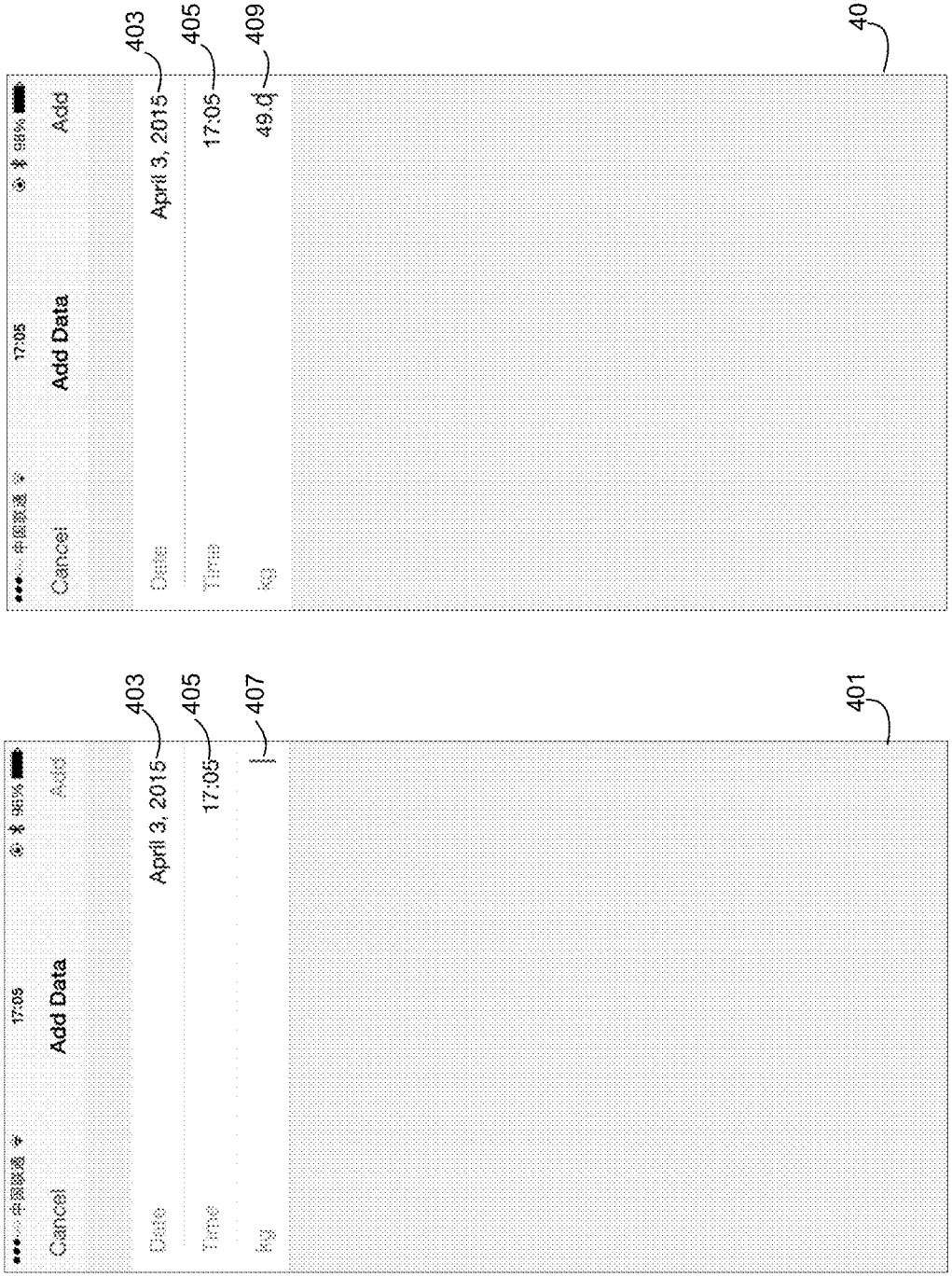

PHYSICAL PARAMETER SENSING SYSTEM

CROSS-REFERENCE TO RELATED APPLICATIONS

This application is a continuation of co-pending U.S. patent application Ser. No. 15/094,609, filed Apr. 8, 2016, the entire contents of which are incorporated herein by reference for all purposes, which claims the benefit of priority under 35 U.S.C. § 119(e) to U.S. Provisional Application Ser. No. 62/145,911 filed Apr. 10, 2015, which is incorporated by reference herein in its entirety for all purposes.

FIELD OF THE INVENTION

This application relates to measurement devices and transmission devices. In embodiments, the application relates to weight measurement devices.

BACKGROUND OF THE INVENTION

Smart sensors and other devices collect real time data and may provide input data streams to receiving processing devices such as: personal computers or mobile telephones or tablets, computer applications, web applications, or cloud based programs and systems. These input data streams may be transmitted through wired or wireless communication links, such as wireless communications implemented using standard protocols such as one of the BLUETOOTH® protocols.

Typically, a receiving processing device is enabled to process data transmitted from these sensors and devices by a bridge application program ("app") or a dedicated app to process the data on the receiving processing device. In either case, the app is in the form of software that must be downloaded and installed on the receiving processing device. In many cases, the app is specific to one device or sensor.

Measuring devices are available for sensing various physical parameters. The measuring device includes one or more sensors which measure the physical parameters. The sensors produce signals that are processed to produce a value representative of the physical parameter in a desired format. The processed physical parameter may then be provided to a display and shown to the user. Additionally, with the advance in computing technology and mobile computing, applications are available which receive data relating to physical parameters and provide a user with a means of tracking physical parameters over time. These applications, or apps, may analyze the received physical parameter data and provide a user with additional information about the physical parameter, or may provide other information or coaching to a user who seeks to monitor or control the levels of the tracked physical parameters. The user may manually enter the physical parameter displayed on the measuring device into the app. The app may be running on, for example, a mobile device such as a smartphone. For example, a user wishing to track his or her body weight, could install a fitness tracking app on their mobile device. A data input screen provided by the app software provides input fields for the user to select and manually enter information via a hardware or virtual keyboard. The user views their body weight as measured by the sensing or measurement device (scale), for example, from a display on the scale, and manually types or enters the displayed information into the app. The app saves the information for later retrieval or additional processing such as tracking or other fitness functions. However, this type of manual data entry is inconvenient and demands the attention of the user. In addition, manual data entry is subject to input errors, which may affect the accuracy and usability of the entered data.

Measuring devices may be linked to a remote processing device having specialized software installed which perform functions such as weight tracking, fitness tracking and management along with other fitness-related functions. In order to implement a link between such a measuring device and a processing device, the measuring device must identify itself to the processing device. Once identified, the measuring device transmits data to the processing device in a format determined by a set of rules established by the processing device. For example, an application (app) running on a mobile device may provide an Application Programming Interface (API), which provides descriptions of the data that the app may receive, and provides abstractions of data processing functions that may be performed on the received data. For example, an abstraction of a data processing function in the API, may include a method called "updateParameter( )". The updateParameter method may be called at the processing device and includes a new value of the physical parameter measured by the measuring device. The user need not know the specifics for updating the value in the processing device or app running on the processing device. Instead, the API provides the format for the method call that allows the user of the measuring device to call the method with the appropriate input value, and the API will complete the processing of the specifics needed to properly update the value in the fitness app. The measuring device is configured to perform measurements using one or more sensors, process data from the sensors representing the measurements performed, and provide the processed data to an application on the processing device in a format dictated by the API for the app. Generally, a user searches for a specialized app in an online marketplace such as GOOGLE PLAY™, or the APPLE® APP STORE®. The user selects an appropriate app and downloads the app to the user's processing device. The app is designed for interaction with a particular sensing device (e.g. a weight scale), and provides a customized data interface between the app and the sensing device. The downloadable apps may be proprietary, requiring that a particular sensing device receive approval and authorization for compatibility and access to the application program interfaces (APIs) that were used to implement the software in the app.

Sensing devices that operate with a broad range of apps and overcome the disadvantages of manual data entry are desired.

SUMMARY

A sensing apparatus according to an embodiment of the disclosure for measuring at least one health and fitness parameter includes at least one sensor for detecting at least one health and fitness parameter and outputting a signal representative of the parameter. The sensing apparatus includes a memory for storing data and computer instructions, and a communication component configured to transmit data representative of the at least one health and fitness parameter. A processor in the sensing apparatus communicates with the at least one sensor, the memory and the communication component. The processor receives output signals from said at least one sensor and calculates at least one health and fitness parameter based on computer instructions stored in the memory. The parameter is provided to the communication component, which transmits the parameter formatted in a human interface device (HID) or other input device compliant protocol to a remote processing device.

A method according to an embodiment of the disclosure for providing a health and fitness parameter value from a sensing device to a remote processing device includes the steps of: detecting at a sensor of the sensing device, an aspect of a health and fitness parameter value; outputting from the sensor, a signal representative of the health and fitness parameter value; receiving at a processor of the sensing device, the signal output by the sensor; processing the output signal to calculate a health and fitness parameter value; converting the calculated health and fitness parameter in a human interface device (HID) compliant protocol; providing the HID compliant health and fitness parameter value to a communication component of the sensing device; and transmitting, at the communication component, the HID compliant health and fitness parameter value to the remote processing device.

BRIEF DESCRIPTION OF THE DRAWINGS

FIG. 4A and FIG. 4B are exemplary screen displays of a processing device showing the entry of health and fitness data to an application on the processing device according to an embodiment of the disclosure.

DETAILED DESCRIPTION

Figure 1:
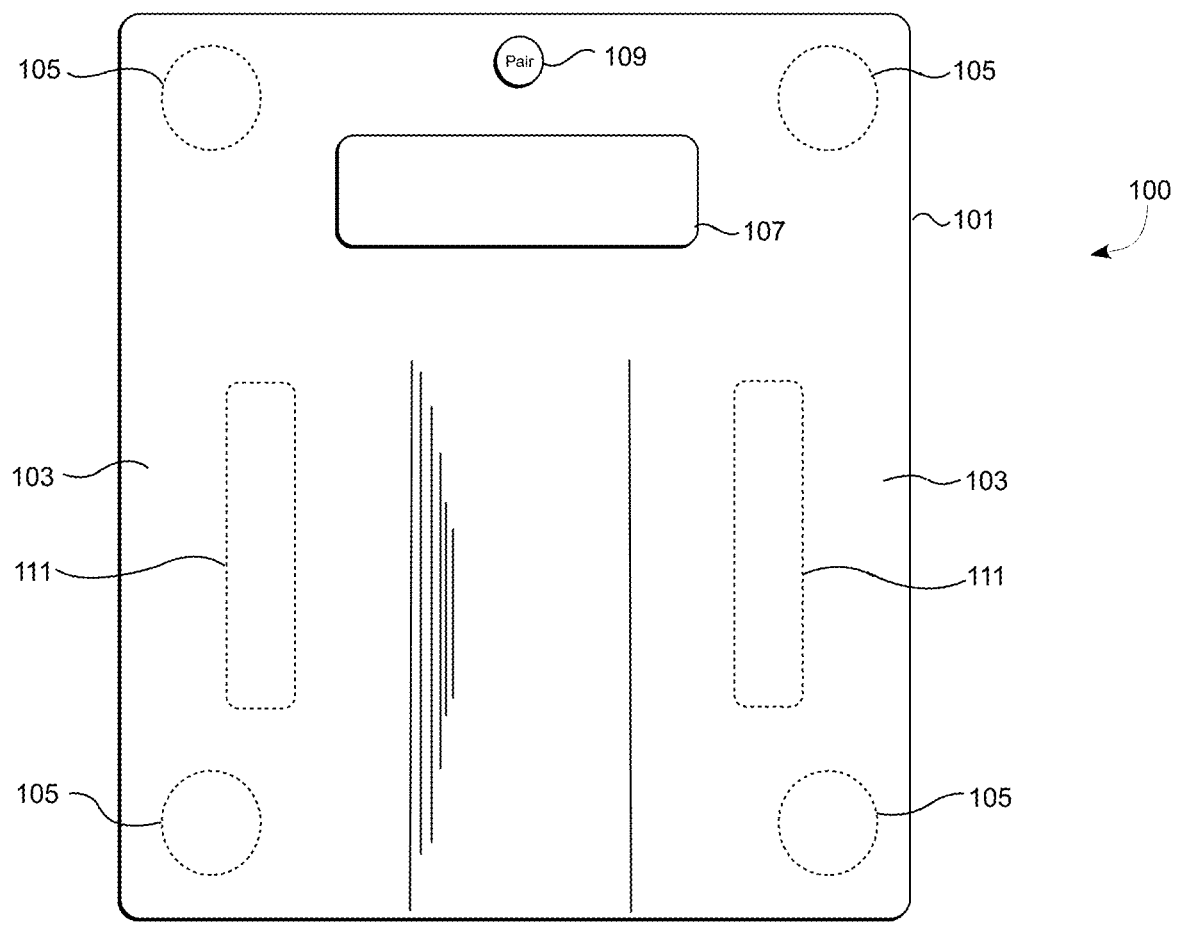
FIG. 1 is an illustration of a health and fitness sensing device according to an embodiment of the disclosure.

It is to be understood that the figures and descriptions of this disclosure have been simplified to illustrate elements that are relevant for a clear understanding of the disclosed subject matter, while eliminating, for purposes of clarity, many other elements found in typical electronic data storage, data transfer systems and health-related sensors and equipment. However, because such element may be well-known in the art, or because they do not facilitate a better understanding of the subject matter, a discussion of such elements is not provided herein. The disclosure herein is directed to all such variations and modifications known to those skilled in the art.

In the following detailed description, reference is made to the accompanying drawings that show, by way of illustration, embodiments in which the invention may be practiced. It is to be understood that the various embodiments of the invention, although different, are not necessarily mutually exclusive. Furthermore, a particular feature, structure, or characteristic described herein in connection with one embodiment may be implemented within other embodiments without departing from the scope of the invention. In addition, it is to be understood that the location or arrangement of individual elements within each disclosed embodiment may be modified without departing from the scope of the invention. The following detailed description is, therefore, not be taken in a limiting sense, and the scope of invention is defined only in the appended claims, appropriately interpreted, along with the full range of equivalents to which the claims are entitled. In the drawings, like numerals refer to the same or similar functionality through several views.

Embodiments of the disclosure provide an apparatus for measuring and tracking physical parameters, including but not limited to fitness and health information, such as weight, body impedance, body fat or body water composition. In addition, additional sensors measuring non-health related parameters may be included. By way of example, certain embodiments of the disclosure may include an apparatus that measures and tracks distances walked or run, global positioning system (GPS) related data, among other non-physical parameter data. Some embodiments may incorporate sensors that include: temperature sensors, pressure sensors, acclerometers, optical sensors, position sensors, displacement sensors and force sensors. These embodiments would include a processor compatible with the type of sensor or sensors being used and be configured to process and validate data received in signals from the sensors and communicate the validated data to a communications component. The communications component may include a transmitter and receiver for sending and receiving data via a wireless communications protocol. The wireless communications protocol may be a short-range wireless communications protocol. For example the wireless communications protocol may comply with the BLUETOOTH® communication standard. The apparatus may be configured to sense the fitness or health information, process and store the information, and display a value associated with the sense fitness or health information. The apparatus formats the measurement values in a HID or other input device compliant format and transmits the compliant data values to a remote processing device. In an embodiment, the other processing device may be a mobile device, such as a mobile phone. However the processing device is not thus limited. The other processing device may be any computing device having a compatible processor. As the HID protocol is defined as part of the Universal Serial Bus (USB) specification, any computing device, such as a smartphone, tablet, laptop computer, netbook, or desktop computer configured to interface with a USB interface could be used. Furthermore, any operating system which supports the USB specification could receive the HID compliant information. For example, processing devices running a WINDOWS® operating system, MAC® OS X° operating systems, LINUX®, UNIX®, or ANDROID™ and IOS® mobile operating systems among others may be configured to be compatible with the HID compliant health and fitness data. The other processing device receives the processed information as input in HID format, in a manner similar to receiving input from a keyboard or other human interface device. Therefore, the other processing device does not need a bridge application or other software particularly configured to receive data from a particular class of sensing device to receive the fitness information from the apparatus. In this way, the user may easily track his or her fitness level without having to install additional software, or to input the fitness or health information into the other processing device manually; the data is input to the processing device automatically by the apparatus. The user may simply operate the apparatus to obtain a fitness information measurement. The apparatus processes the measurement values provided by the sensors, and formats the processed information into an HID format representative of the health and fitness information. The HID compliant data is then transmitted to the processing device which is configured to receive the HID compliant data based on the HID protocol provided by the operating system of the processing device. The other processing device may further process the received fitness or health information to create and/or alter a fitness program to achieve desired goals based on the received fitness and health information. In prior applications, the establishment of communication between the processing device, or application software running on the processing device, and the apparatus for measuring and tracking physical parameters required specialized software customized to provided communication between the apparatus and the processing device. For example, when the apparatus measured a health or fitness parameter and needs to transmit the information to the processing device, the information would need to be packaged or formatted to the class definitions in an API. Thus, the designer of the apparatus would need to know a priori the class definitions in the API specific to a particular application on the processing device. If the apparatus was intended for use with more than one application, it may become necessary to process the information differently for each application with which the apparatus intends to communicate. This provides additional front end design and processing at the sensing apparatus to remain compatible with a wide array of devices and applications. Furthermore, the communication must occur between the application interfaces of two different providers. Mistakes occurring on either end of the communication path, with regard to the interface definition, or errors in processing the data increase the opportunity for bugs to appear in the code for communicating the fitness data. If the data is not readily compatible with the API specification for a given application, a bridge application may need to be designed and coded to process the data for compatibility. The bridge application receives the fitness data and stores the fitness data on the remote processing device. The remote processing device may then perform additional processing on the received and stored fitness data. Should the processing in the application on the processing device, or the processing of the health and fitness information on the sensing apparatus need to changed, the bridge app would need to be updated and additional programming time would be needed to maintain compatibility. The requirement that a bridge app be used also creates the need for the designers of the sensing apparatus and the designers of processing device or application to remain aware of when the other party updates or changes their product. These updates or changes could affect the transfer of data between the sensing device and the remote processing device. In embodiments, the use of HID or other input device compliant data provides communication of the fitness data using an interrupt request priority at the remote processing device equivalent to the interrupt request priority used by an input device such as a keyboard or mouse. The interrupt request is provided to the processor of the remote processing device. The processor will store the incoming fitness data, wait for current processing to complete, and place all other queued processing tasks having a lower priority than the interrupt request on the system stack. While the other processing tasks are on the system stack, the data processing request provided with the interrupt is processed. Once the interrupt request is completed, the queued processes are taken one by one from the system stack and processing of these tasks resumes. Processing tasks typically used in applications such as a bridge app would have a lower priority than the interrupt priority associated with the HID or input device compliant fitness data. The fitness data is provided to the processing device in a format that is readily received and in a format defined at the input device level, allowing the data to be quickly and accurately input to the application through an interface compatible with a basic input device.

Referring now to FIG. 1, an exemplary apparatus 100 for sensing, processing, displaying and transmitting fitness and health information is shown. The apparatus 100 may include a scale 101 for measuring the body weight of a person using the apparatus 100. Apparatus 100 further includes processors, circuitry, communications components and displays, by way of example. Scale 101 has one or more load cells 105 for determining the weight of the user. Load cells 105 are on deflectable members. Load cells 105 include strain gauges, which may be one or more variably responsive resistors on a portion of the members that deflects and provide an output dependent on deflection of the member when a force is applied to the deflectable member.

A circuit may be connected to the variably responsive resistors of load cells 105. A controlled voltage may be applied to the circuit. The current through the circuit generated by the voltage will vary dependent on the resistance exhibited by the variably responsive resistors of the load cells 105, which is in turn dependent on the load being applied to the load cells 105. The scale 101 includes a platform 103, which supports an individual whose weight is being measured. The platform 103 rests on load cells 105, which in turn, are supported by the body of scale 101. In addition to load cells 105, scale 101 may include additional sensors for measuring other body parameters. For example, scale 101 may include one or more electrodes 111, which are configured to contact the body of the individual being weighed. An electrical voltage is applied to the electrodes 111 which generate an electrical current between the electrodes by passing through the individual's body. As electrical current passes more easily through lean muscle than through body fat, and the percentage of water in body cells affects the resistance and reactance of the impedance measured at electrodes 111, the measured impedance may be used to calculate health parameters, for example, body mass index (BMI), body fat percentage, body water percentage, etc., according to algorithms and processing known in the art.

In the context of weight measurement, a person stands on the platform 103 of scale 101. The weight of the person causes the platform 103 to deflect and exert a force on load cells 105. A signal indicative of the force being applied to the load cell 105 is provided to a processor of scale 101. The signals from all load cells 105 of scale 101 are processed to determine the weight of an individual standing on the platform 103. When the processor of scale 101 determines the weight applied to platform 103, the weight value is output by the processor to display 107 and displayed by display 107. Display 107 may be a liquid crystal display (LCD), light emitting diode (LED), organic LED (OLED) or other display type, which is configured to receive an electrical signal representative of a sensed weight value and to display a numerical value based on the received signal. The numerical value provided in the signal may be converted to display one or more numerical values associated with a selectable weight unit. By way of non-limiting example, the weight value represented in the received signal may be converted and displayed in units of pounds (lbs.), stone (st) or kilograms (kg.).

Scale 101 also includes a pairing button 109. When a user presses and holds pairing button 109, a wireless pairing process is performed between scale 101 and another processing device (not shown). Scale 101 shows the use of a push button to initiate pairing of the scale to a remote processing device, however this is provided by way of example only. Initiation of pairing or pairing may be performed by other processes as well. For example, scale 101 may include a user accessible menu system where menu options are provided to the user through display 107. One menu option may include pairing the scale 101 to the remote processing device. When this menu option is selected by a user, the scale may perform a broadcast operation to indicate that scale 101 is available for pairing to a remote device. An available remote device will be able to detect the broadcast indicating the scale 101 is available for pairing. Navigation buttons associated with the display 107 may be provided on the upper surface of the scale 101 to allow the user to navigate and select various menu options. It is also understood that any other suitable interface may be provided which allows the user to indicate the availability of the scale 101 for pairing with a compatible remote processing device. The pairing process may be performed according to the BLUETOOTH® standard for pairing devices. The communication link between the other processing device and scale 101 may be achieved through a wireless communication protocol. For example, wireless communications through a BLUETOOTH® protocol compliant or Bluetooth Low Energy (BLE) protocol compliant communication link may be used. Other wireless communication protocols may be used, such as wireless communications under IEEE 802.11, which includes wireless communications using WiFi or other short-range wireless communications protocols.

Figure 2:
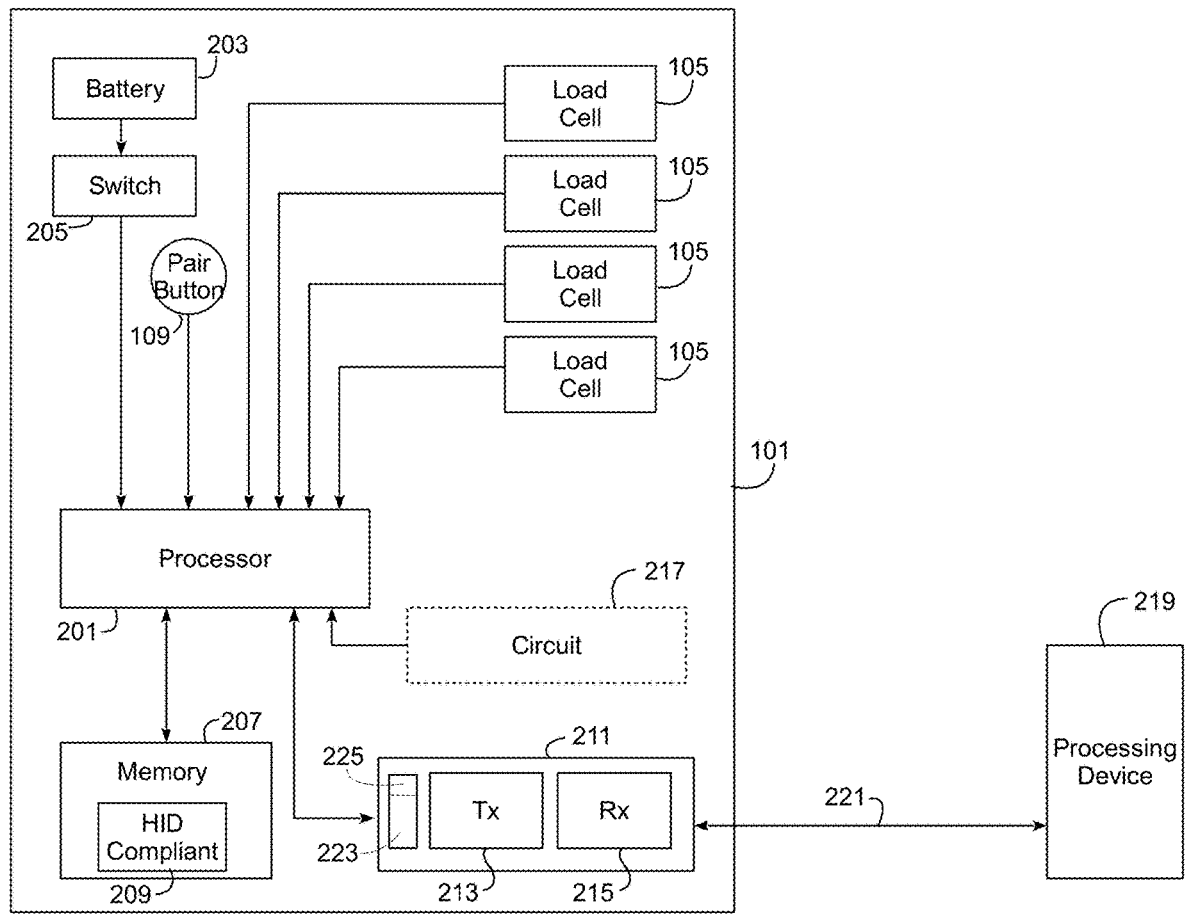
FIG. 2 is a block diagram illustrating selected portions of the health and fitness sensing device of FIG. 1.

FIG. 2 is a block diagram of scale 101 of FIG. 1. Scale 101 includes a processor 201 in communication with a memory 207. Processor 201 is coupled to sensors, including load cells 105. Load cells 105 may be positioned to support platform 103 shown in FIG. 1. Processor 201 may also be coupled to circuit 217. Circuit 217 may be in communication with other sensors or measuring devices, such as electrodes 111 shown in FIG. 1, which apply an electrical current to the body of a person being weighed to measure the impedance through the person's body. Circuit 217 may include a memory containing software instructions that when processed by a processor (e.g. processor 201, or another processor associated with circuit 217) cause the processor to calculate a health or body parameter and to communicate the calculated parameter to processor 201. In an embodiment, processor 201 may have an associated memory for storing software instructions that may be processed by the processor 201. For example, circuit 217 may be configured to calculate and communicate a BMI value, or a body water percentage, by way of non-limiting example.

A circuit may be connected to the variably responsive resistors of load cells 105. A controlled voltage may be applied to the circuit. The current through the circuit will vary dependent on the resistance being exhibited by the variably responsive resistors of the load cells 105, which is in turn dependent on the load being applied to the load cells 105. The current may be used to produce a sensor signal indicative of the load being applied to the load cell. The signal is converted to a digital signal in an analog to digital converter (ADC) and provided to processor 201. Instructions may be stored in memory 207 which when executed by the processor cause the processor to process the received signal. For example, the signal provided by the load cells may be converted by processor 201 executing software instructions to produce a numeric value. Based on user settings set in the scale 101, the numeric value may represent the weight of a user. The numeric value may represent the user's weigh in kilograms, pounds or stones. The stored software instructions process the input signal to produce the appropriate numeric value based on the user-defined settings. Memory 207 may include further instructions, which further process the numeric value derived from the load cell 105 signals. For example, software instructions may be configured for execution by processor 201 to perform data validations on the numeric value. For example, a weight scale would not be expected to measure weight as a negative value. Therefore, instructions within memory 207 may check the numeric value to ensure that the numeric value is non-negative. Furthermore, load cells 105 may have specific operating ranges. The numeric value may be validated to make sure that the numeric value produced from the load cell 105 signals falls within the appropriate range. Other validations, such as proper decimal values (e.g., the value contains no more than one decimal point, or an expected number of decimal places) may be performed. Once the numeric value is validated, it may be processed to be converted into proper HID or other input device compliant form and provided to BLUETOOTH® communications component 211 for transmission to processing device 219.

Processor 201 is in communication with BLUETOOTH® component 211 and may produce a signal, which instructs the BLUETOOTH® component 211 to power on, including the radio portion of BLUETOOTH® component 211. Processor 201 may be configured to turn off the BLUETOOTH® component, including the radio portion at times when the load cells 105 are sensing data and providing that data to processor 201. Some sensors, such as load cells 105 may operate on the level of microvolts. The power generated by the BLUETOOTH® component 211 radio may create significant interference, which may corrupt or completely block the signals from sensors such as load cells 105. For this reason, the processor 201 may be configured to turn off the BLUETOOTH® component 211, in particular the radio portion, while processing of the sensor signals is being performed. When the sensor signals are processed and validated by processor 201, the processor will convert the processed value to an HID compliant value and provide the validated and converted value to the BLUETOOTH® component 211. Prior to providing the validated, converted value, processor 201 may send a wake signal to BLUETOOTH® component 211 to turn the component on and to power on the radio portion of BLUETOOTH® component 211, including transmitter 213 and receiver 215.

Scale 101 may receive power to operate via an internal power source such as battery 203. Power may also be supplied by an external power source, such as an external battery, or by AC power, such as household voltage, via an AC adapter (not shown). A switch 205 between power source, (e.g. battery 203) and processor 201 may be used to conserve power when scale 101 is not in use. Switch 205 may be a mechanical switch, which is operated by the user. Alternatively, switch 205 may be operable by motion or vibration, allowing the user to turn on switch 205 by stepping on scale 101 or by tapping on platform 103 shown in FIG. 1. Processor 201 may be configured to enter a low power sleep mode within a certain time period after detecting a zero weight.

Pairing button 109 is coupled to processor 201. When pairing button 109 is pressed by a user, a signal is sent to processor 201. Processor 201 accesses memory 207 and retrieves software instructions stored in memory 207. The received software instructions cause processor 201 to perform a wireless communication pairing process. The pairing process creates a communication link 221 between scale 101 and another processing device 219. For example, processor 201 may, in response to the execution of software instructions stored in memory 209, send operation instructions to communication component 211. Communication component 211 may be implemented in hardware, software or a combination of hardware, firmware and/or software. For example, communication component 211 may be a BLUETOOTH® component including a processor, transmit/receive antenna and radio for transmitting and receiving BLUETOOTH® communications. Communication component 211 may be a wireless communication component, which is configured to initiate, establish and maintain a wireless communication link 221 between scale 101 and processing device 219. Communication component 211 includes a transmitter module 213 and a receiver module 215 for establishing two-way communications between scale 101 and processing device 219. According to one embodiment, communication component 211 may conduct wireless communications via a BLUETOOTH® communication protocol according to the BLUETOOTH® standard established by the Bluetooth Special Interest Group (SIG) Inc. headquartered in Kirkland, Wash. Communication component 211 includes a processor 223, which may be implemented as a reduced instruction set computing (RISC) processor. The RISC processor 223 has a core 225, which includes memory space for embedding within the firmware of the communication component 211, product specific information relating to the sensing apparatus 101. For example, product specific information embedded in the core 225 of RISC processor 223 may include an identifier (e.g. MAC address), an identifying label providing a descriptive name of the specific product or device, and information identifying the data format of the data being transmitted by the communication component 211 as explained in greater detail with reference to FIG. 2A.

Figure 2A:
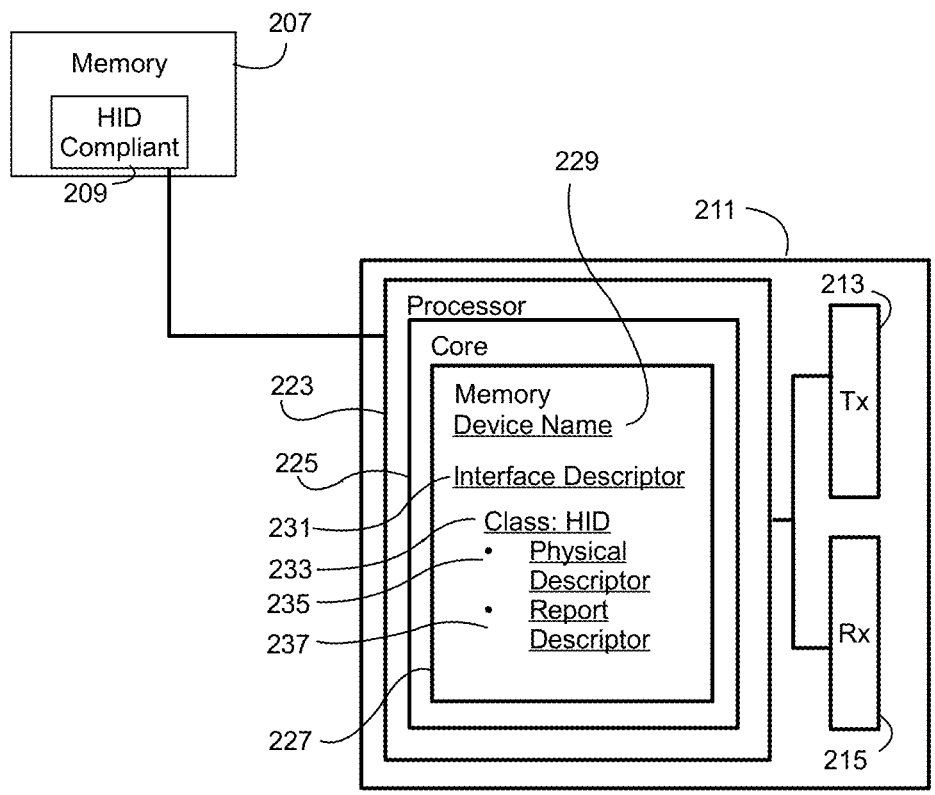
FIG. 2A is a block diagram of a communications component of the health and fitness sensing device of FIG. 1 according to an embodiment of the disclosure.

Referring now to FIG. 2A, the health or fitness information may be processed and stored in memory 207 of apparatus 100 shown in FIG. 1. The health and fitness information may be processed as input from sensors, which measure health and fitness information, such as a physical parameter and perform processing on the received input. For example, validation processes may be performed on the input received from the sensors. Further, the information may be formatted into a particular format for display or communication to a remote processing device. Apparatus 100 also includes a communications component 211, which is in communication with memory 207. Communications component 211 includes processor 223, which may be implemented as a RISC processor. Processor 223 includes a core 223 which further includes memory 225 embedded within processor 223. Memory 225 may be programmed to store information used by processor 223. By way of example, memory 225 may contain descriptive information for the device or apparatus 100, which contains the communications component 211. For example, descriptive information may include a descriptive label indicative of the device name 229. The device name 229 may be provided to a remote processing device to indicate to a user, the name of apparatus 100 which is attempting to pair for communications with the remote processing device. Further, memory 227 may include additional information relating to the interface descriptor 231 associated with the data to be processed by processor 223 and transmitted via transmitter 213. Interface descriptor 231 may indicate one or more classes available for transmission via the communications component 211. In an embodiment, the interface descriptor 231 indicates the defined class 233 of Human Interface Devices (HID). The interface descriptor 231 identifies a class. The class divides functions of a USB device that have similar data transport requirements and share a single class driver. For example, the HID interface class will generally provide data that could be generated from an input device such as a keyboard, mouse or joystick. The data will be handled at the remote device by a HID driver. The HID class descriptor may identify further class descriptors and their corresponding sizes. For example, the HID class description 233 may include additional descriptors such as a physical descriptor 235 or a report descriptor 237. A report descriptor 237 describes each piece of data that the device generates and what the data is actually measuring. The HID report descriptor 237 may be sent to an HID driver installed on the remote device. The HID driver software may read the HID report descriptor 237 and determine the size and composition of data in the report descriptor 237. An HID class device communicates with the HID class driver by the Control pipe by default. The Control pipe is used for receiving and responding to requests for USB control and class data; transmitting data when polled by the HID class driver (e.g. using the Get_Report request); and receiving data from the host. The Control pipe is always present in USB devices (e.g. HID devices) and provides low-level access to the operating system of the remote processing device. Access to the operating system is controlled through interrupt requests (IRQs). IRQs have priorities associated with them, which allow the operating system to prioritize processing tasks associated with each interrupt request. Based on the interrupt request's priority, other processing tasks may be queued and placed on the system stack for processing after the current interrupt request has been handled by the system processor. When the current interrupt request has been processed, the queued tasks are taken from the system stack one by one and processing continues. Access to the remote processing device via the Control Pipe allows the health and fitness apparatus 100 to transmit data to the remote processing device, using the HID interrupt associated with a relatively high system priority. This higher priority associated with the HID interrupt level also allows functionality such as waking the remote processing device from an idle or sleep mode when new data is received from the health and fitness device.

By way of example, the data format may indicate the data is represented as text, such as would be entered by a keyboard. The data format may further indicate the data is to be provided to the remote processing device 219 via an input port reserved by the operating system (OS) of the remote processing device for keyboards. An input port reserved for keyboard input data may have interrupt levels or priority settings, which prioritize the data received at the keyboard port in relation to other device inputs or application requests.

According to one embodiment, scale 101 may use processor 223 of the communication component 211 for processing the health and fitness parameter based on an output of load cells 105. In this embodiment processor 201 may be omitted. One or more analog to digital converters (ADCs) may be placed between the load cells 105 and the communication component 211 to provide digital signals to the processor 223 in the communication component 211. At least one health and fitness parameter value is calculated based on the digital signals. The calculated health and fitness parameter value is formatted in a HID compliant format and transmitted via communication link 221 to the remote processing device 219.

Memory 207 is configured to store software programs or instructions that are executable by processor 201 and that when executed by processor 201 cause the health and fitness metrics (e.g. a sensed weight, calculated based on the output of load cells 105), to be formatted in a particular protocol or structure, which is useable by processing device 219. For example, the output of the load cells 105 may be processed to validate the sensor output. In the case of a weight scale, the output signal is representative of a measured weight value. The output signal should not indicate a negative value for weight as such a value is meaningless with respect to weight. Furthermore, the load cells and associated sensors may have designed ranges in which they operate. The health and fitness device may include a computer memory storing parameter values to which the output signal values may be compared. In some embodiments, validation processing may also include a check to ensure the output signal of the sensors falls within the expected design range. Additionally, the heath and fitness device may allow the user to select a unit of measurement. In the case of a weight scale, the weight may be indicated in pounds, kilograms, or stone. The data stored in memory 207 may be processed to represent a value in the user-specified units of measurement. To provide the data to the remote processing device, the data may be further processed to match the interface descriptor specified in the communications component 211. For example, an HID class descriptor may receive the processed HID compliant data in a form or format consistent with a keyboard or other forms. The measured physical parameter values (e.g. weight) are converted by the device processor 201 to a series of character data (or keyboard keystrokes). This data may be packaged in a report descriptor and provided to the HID driver in the remote processing device. According to an embodiment, the protocol or structure is not specific to a software program or application running on processing device 219, but rather is provided in a general format that is compatible with a basic input/output (I/O) format used by processing device 219. By way of example, FIG. 2 illustrates that data relating to the health metric information may be stored in memory 207 as Human Interface Device (HID) compliant data. The HID standard is a Class Definition established by the Universal Serial Bus (USB) Implementers Forum, Inc of Portland, Oreg., which defines a communications architecture allowing interconnection of computers with a variety of other devices classified as HID devices. Typical examples of HID devices include keyboards and pointing devices such as keyboards, mice, trackballs or joysticks, front-panel controls such as knobs, switches, buttons or sliders, and device specific controls such as game controllers including data gloves, throttles, steering wheels, and rudder pedals. Other devices, which do not require human interaction, but provide similar data in a similar format to HID class devices may also be implemented using the HID Class definition. Examples of non-interactive devices may include bar-code readers, thermometers or voltmeters.

Processor 201 executes instructions stored in memory 207 to format health and fitness parameters data calculated by processor 201 within scale 101 and adapts the health and fitness parameter data to comply with the HID device class definition. The HID compliant information may be communicated to the processing device 219 over communication link 221 from communication component 211.

The process of establishing wireless communication link 221 will now be described for an embodiment using the BLUETOOTH® wireless communication standard with reference to FIG. 2 along with FIGS. 3A, 3B and 3C.

Figures 3A, 3B, 3C:
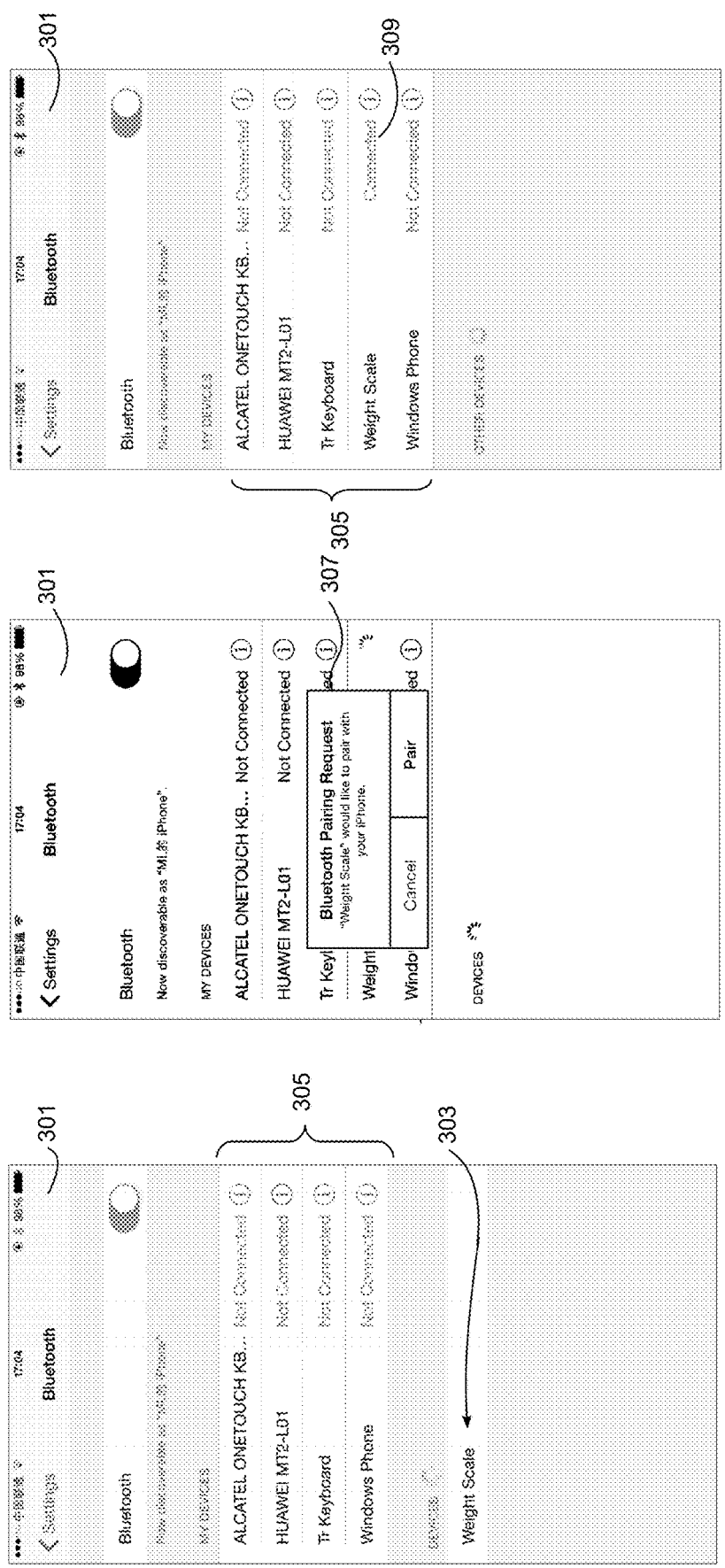
FIG. 3A, FIG. 3B and FIG. 3C are exemplary screen displays of a processing device showing the establishment of a communication link between the health and fitness device of FIG. 1 and the processing device.

FIG. 3A shows an exemplary screen display of processing device 219. For example, processing device 219 may be a mobile phone, such as an iPHONE® manufactured by Apple Inc. of Cupertino, Calif. To begin the pairing process, the user of scale 101 depresses pairing button 109 and holds down pairing button 109 for a period of about 3 seconds or more. Requiring the user to hold pairing button for at least about 3 seconds prevents scale 101 from initiating a pairing process in cases where the user momentarily presses pairing button 109 through incidental contact without the desire to start the pairing process. Pairing button 109 sends a signal to processor 201 to begin the pairing process. Processor 201 sends a command to communication component 211 to begin transmitting the identity and the availability of scale 101 to establish a communication link 221. The user of processing device 219 navigates to the settings application on the processing device 219. The settings application manages connections to the processing device 219 via the chosen communication protocol (i.e. setting). For example, in the illustration shown in FIG. 3A, the communication protocol is BLUETOOTH®. The BLUETOOTH® settings screen 301 displays a list of devices 305, which are recognized by the processing device 219 by virtue of the processing device 219 having previously connected to the displayed devices. In addition, the settings screen 301 also displays other devices, which are not known to the processing device 219, but are broadcasting their identity and availability for establishing a communication link 221 via BLUETOOTH®. As seen in FIG. 3A "weight scale" is displayed, indicating scale's 101 identity "Weight Scale" and availability for communication.

The user may touch or click on the "weight scale" label and begin initiating a communication link with scale 101. A dialog box 307 containing a confirmation message and response buttons is presented to the user as illustrated in FIG. 3B. The dialog message indicates that "Weight Scale" would like to pair with the processing device 219 and provides response buttons that allow the user to select between establishing the connection (e.g. via the "Pair" button), or to ignore the request via the "Cancel" button.

If the user opts to establish a communication link 221 with the weight scale 101 by touching or clicking the "Pair" button, the weight scale is added to processing device's 219 list of known devices 305 as shown in FIG. 3C. The weight scale 101 and the device are now paired. When a communication link between the two paired devices is active, a status indicator of "Connected" is displayed indicating the communication link 221 between the scale 101 and the processing device 219 has been established and is currently active.

Once a communication link 221 has been established, data measured and processed by scale 101 may be transmitted via communication link 221 to the processing device 219. The data may be formatted according to a specification such as the HID Class Definition, by way of example. Formatting the data according to a data architecture such as the HID Class Definition allows for scale 101 to communicate with processing device 219 at a basic I/O level. In other words, processing device 219 does not need to rely on additional processing by software or apps installed on processing device 219 in order to receive and use the health metric data from scale 101. As a result, scale 101 does not need to be associated with a custom software app installed on the remote processing device. The information provided by scale 101 is readily accessible and available to processing device 219 without additional software or processing. Scale 101 transmits the health metric data in HID compliant format allowing virtually any application running on processing device 219 to receive and accept the health metric data as a basic input. The process of receiving health metric data in a HID compliant format is illustrated as shown in FIGS. 4A and 4B with reference to scale 101 of FIG. 2.

FIG. 4A is an exemplary display screen of processing device 219 displaying a data entry screen 401. The data entry screen 401 may be associated with any software application, as indicated by the generic identifier "Add Data" shown at the top of the screen in FIG. 4A. The data entry screen 401 contains three data fields associated with a date 403, a time 405 and a weight (kg) 407. In FIG. 4A, the values for date 403 and time 405 have been previously entered. Typically, the user touches or clicks the empty text box, which is to contain the entered value. For mobile devices, a virtual keyboard may appear superimposed on the data entry screen 401, allowing the user to select characters for entry into the text box. Depending on the data to be entered, other input objects, such as date/time pickers or other data entry objects may be displayed to the user in place of a standard QWERTY keyboard.

As shown in FIG. 4A, the user may touch or click in the empty text box configured to receive data corresponding to the weight data field, identified by the label "kg". The cursor is positioned within text box 407 indicating the device is prepared to receive data in the selected field. When the device is connected to scale 101 via communication link 221, scale 101 provides data in HID compliant form to device 219 via communication link 221. The HID compliant data is representative of a health and fitness parameter value that is sensed by scale 101 and processed by processor 201 to obtain a value representative of the sensed health and fitness parameter. The HID compliant data is entered into text box 409 as indicated by the value "49.0" shown in FIG. 4B. The user does not need to enter the value "49.0" into text box 409 as this value is provided automatically by scale 101. Using HID compliant data allows the scale 101 to act similarly to a keyboard or other input device, providing the data value to the processing device 219 as if the data was being entered by the user via a keyboard or other input object.

Figure 5:
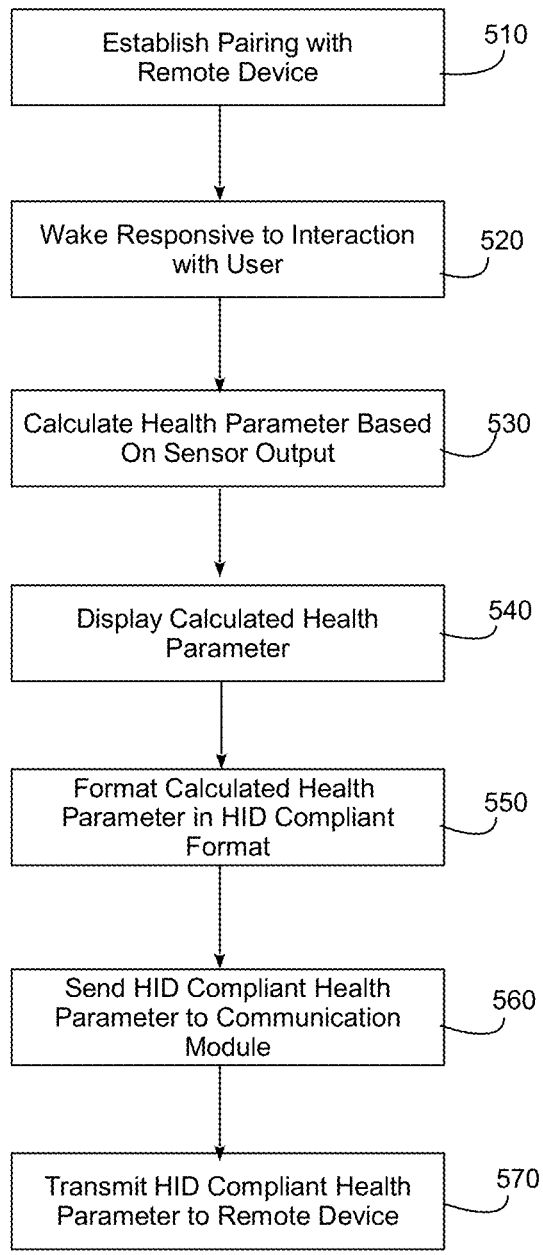
FIG. 5 is a flow diagram of a process performed by a HID compliant health or fitness information from a sensing device, such as the scale shown in FIG. 1, according to an embodiment of the disclosure.

FIG. 5 is a process flow diagram showing the transmission of HID compliant health or fitness information from a sensing device, such as scale 101 shown in FIG. 2. A communication link is established between the sensing device and a remote processing device. The remote processing device may be any type of device for processing health and fitness data. For example, the remote processing device may be personal computer, a mobile processing device such as a mobile telephone, tablet computer, or wearable processing device, such as a watch or fitness band that may be worn by a person. It should be noted that in addition to the remote processing device, the sensing device may also be embodied in such processing devices, provided the device is equipped with sensors and processing capabilities for calculating, formatting and transmitting health and fitness parameters in HID compliant format as discussed herein. The sensing device establishes a pairing with the remote processing device 510 through a process such as the BLUETOOTH® pairing process. During periods of non-use, the sensing device may be configured to enter a standby mode to conserve power. When in standby mode, the device wakes responsive to a user interaction which activates a switch or wake circuit to power on the sensing device 520. The interaction may be tapping on a surface of the sensing device to activate a sensor, such as a pressure sensor, vibration sensor or accelerometer. Once powered on, a processor in the sensing device is configured to receive output data from one or more sensors, which detect one or more health or fitness parameter values and output a signal indicative of the detected values. The sensor outputs may be combined with other sensor outputs to provide data that is representative of a health or fitness parameter value. The sensing device processor receives the sensor outputs and calculates one or more health parameters based on the sensor outputs 530. The calculated health parameters may be displayed to a user at the sensing device 540. For example, in an embodiment where the sensing device is a scale, the processor may receive output signals from one or more load cells. The outputs from the load cells are received by the processor and combined to determine a weight of a load applied to the load cells. The calculated weight is then provided to an appropriate display on the scale (e.g. an LCD display) to display the calculate weight to the user. The sensing device sensors may provide analog signals. The analog signals may be converted by an analog to digital converter (ADC) to a digital signal that is provided as digital data to the processor.

The calculated health or fitness parameter value is formatted by the sensing device processor into a data format that is compliant with the HID protocol 550. The HID compliant parameter value is provided to the communication component and transmitted to the remote processing device 560. In embodiments, the value is generated by the communication component into a format compliant with the HID protocol. The communication component than transmits the HID compliant health or fitness parameter value to the remote processing device.

A sensing device according to embodiments of this disclosure may include one or more types of sensors, which are configured to detect and process information relating to one or more health and fitness parameters. For example, a sensing device may include sensors such as load cells for detecting weight. The sensing device may also include electrodes, which contact the body of a person using the sensing device and supply an electrical current through the body to detect impedance of the body. The impedance provides information about other health and fitness parameters including but not limited to, Body Mass Index (BMI), body water percentage, body fat percentage, body muscle percentage, and bone mass. In embodiments where more than one health and fitness parameter value is sensed and calculated, the set of health and fitness parameters may be formatted in an HID compliant format and provided to the remote processing device as a data stream including each parameter in the set of health and fitness parameters. At the remote processing device, an adapter may be used to assist the user in entering each health and fitness parameter into a corresponding data entry field on the remote processing device. The adapter may be implemented in software installed on the remote processing device and configured to receive a parameter data stream from the sensing device.

Figure 6:
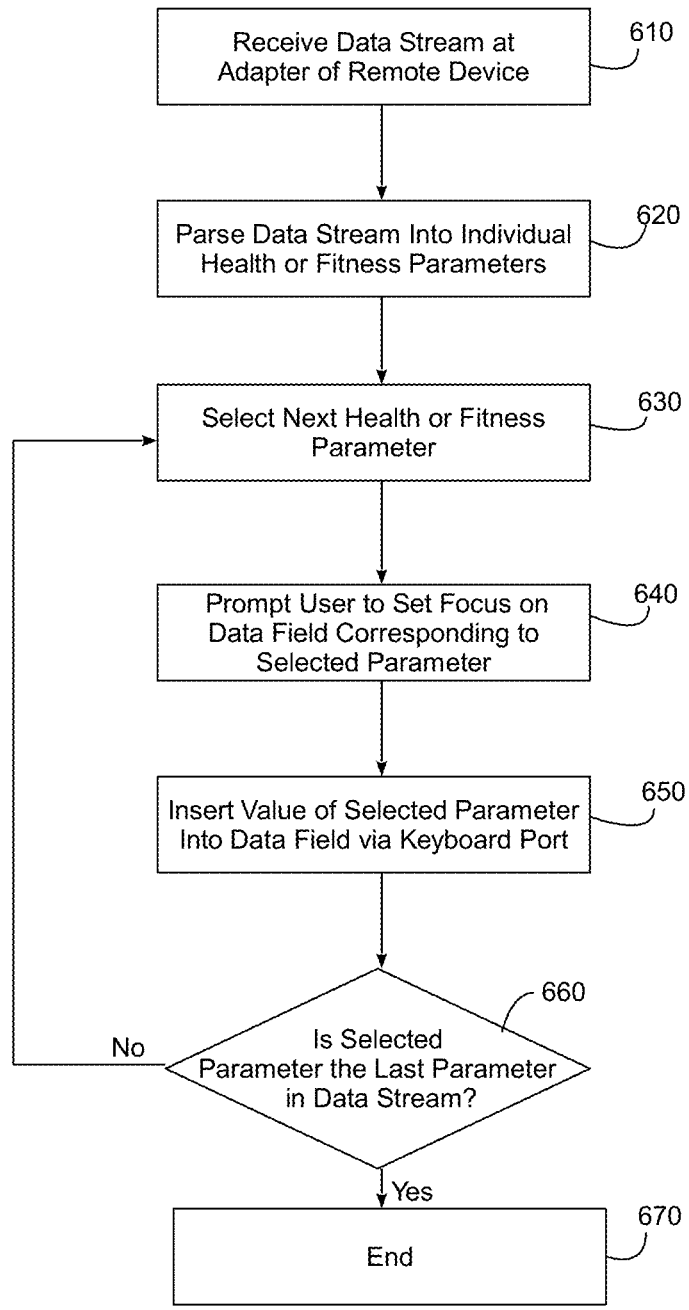
FIG. 6 is a process flow diagram of a process for receiving multiple health and fitness parameters in an HID compliant format and entering the data contained in the data stream at a processing device, according to an embodiment of the disclosure.

FIG. 6 is a process flow diagram of a process for receiving multiple health and fitness parameters in an HID compliant format and entering the data contained in the data stream at a remote processing device. An adapter associated with the remote processing device receives a data stream containing HID compliant health and fitness parameter data 610. The data stream may be received from a sensing device, which is configured to detect and calculate more than one health and fitness parameter, convert the calculated parameters to a HID compliant format and transmit the HID compliant parameter values in a data stream to the remote processing device. The adapter parses the received data stream to identify each health and fitness parameter value contained in the data stream 620. When a set of health and fitness parameters have been identified, the adapter selects a next parameter for entry into a selected application on the remote processing device 630. For example, a user may have a fitness app installed on the remote processing device. The user desires to enter information relating to the user's health and fitness parameters as detected and calculated by the sensing device. The adapter prompts the user to navigate to the data entry screen in the fitness app corresponding to the selected health and fitness parameter extracted from the data stream, and to set focus on the data entry field associated with the selected parameter 640. The user may set focus on the corresponding data field by tapping or clicking on the corresponding data entry field. When the data entry field receives focus, the adapter provides the selected parameter value to the app in an HID compliant format. For example, the adapter may provide the HID compliant data to the app via a keyboard input port in a data format consistent with input from a keyboard. The adapter enters the HID compliant parameter value into the data entry field, which is received by the fitness app 650. Once the selected parameter value has been entered, the adapter determines if the selected parameter is the last parameter in the received data stream 660. If the selected parameter is not the last parameter contained in the data stream, the adapter selects the next health and fitness parameter 640. Otherwise, the process ends when all health and fitness parameters contained in the data stream are entered 670.

Figure 7:
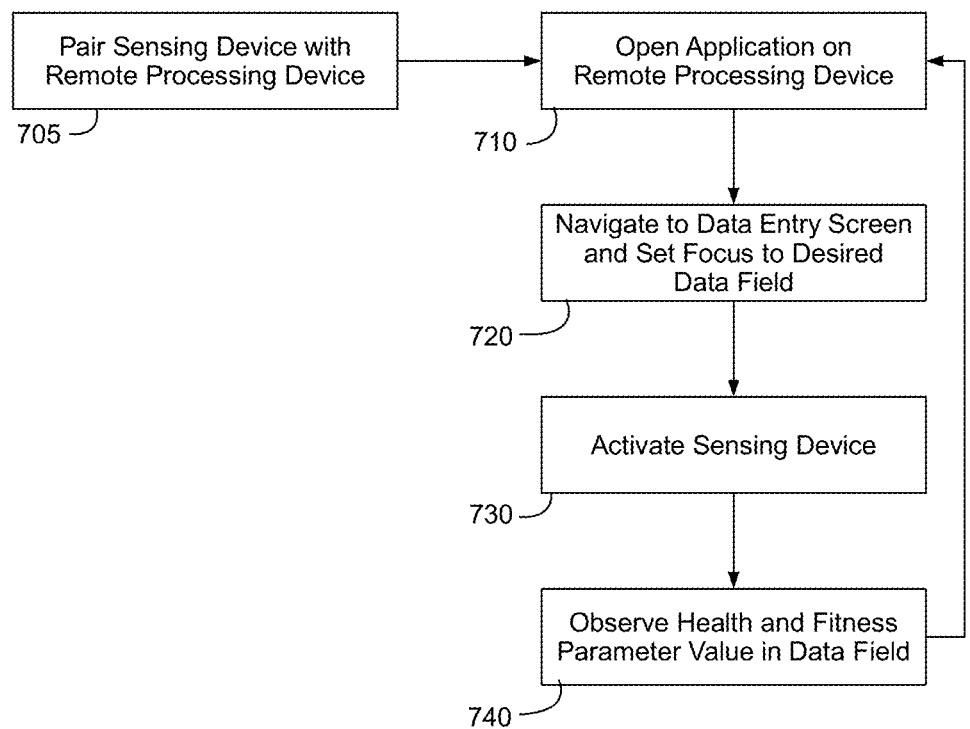
FIG. 7 is a process flow diagram of a process of measuring a health and fitness parameter at a sensing device and inputting the measured parameter in a remote processing device according to an embodiment of the disclosure.

The process of using a sensing device to enter data at a remote processing device will be described with reference to FIG. 7. FIG. 7 is a process flow diagram of measuring a health and fitness parameter at a sensing device and inputting the measured parameter in a remote processing device. Initially, the sensing device is paired with the remote processing device 705. For example, the pairing process may be performed using a BLUETOOTH wireless communication protocol. The pairing process only needs to be performed once to establish a recognized pairing connection between the sensing device and the remote processing device. Subsequent measurements and communications may be performed using the initially established recognized pairing connection without needing to repeat the paring process 705. To enter HID compliant health and fitness data at the remote processing device, a user opens an application on the remote processing device 710. With the application running on the remote processing device, the user then navigates to the data entry screen that is configured to receive the health and fitness parameter value being measured by the sensing device. The user then sets the focus of the app on the remote processing device to the data entry field, such as by tapping or clicking on an editable text field, to receive the sensor device data 720. With the remote processing device now awaiting data entry to the selected data entry field, the user activates the sensor device 730. Once the sensing device has calculated the corresponding health and fitness parameter value, the value appears in the selected data field automatically. The user observes the value in the selected data field 740. The process of entering health and fitness parameter values may be repeated by opening the same or another app on the processing device 710 and repeating steps 720, 730 and 740. The process may be repeated without having to pair the devices again, as the pairing step 705 is only performed one time.

Figure 8:
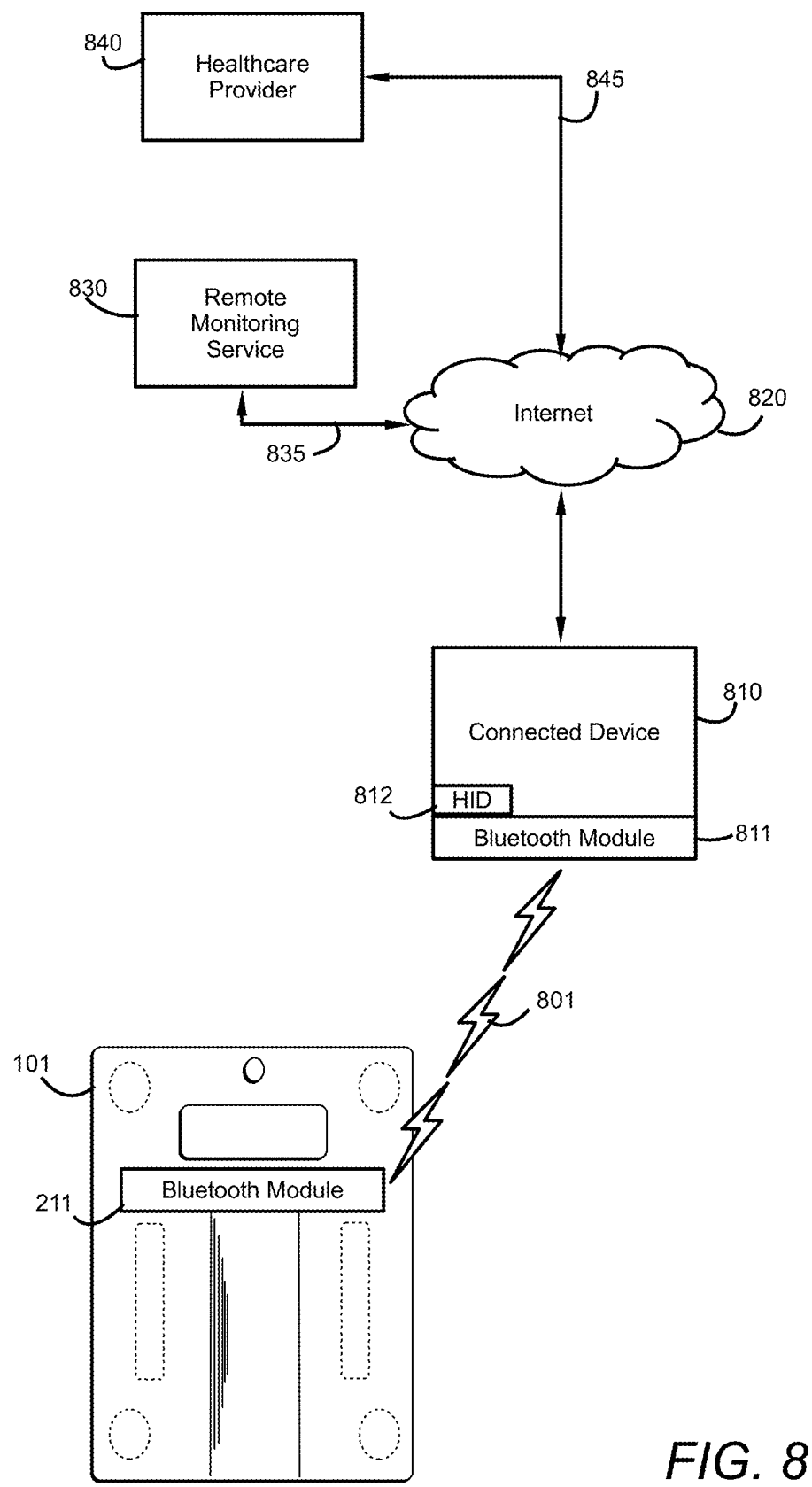
FIG. 8 is a block diagram of a health monitoring system according to an embodiment of the disclosure.

FIG. 8 is a block diagram of a health monitoring system according to an embodiment of the disclosure. FIG. 8 illustrates one practical embodiment in which a sensor device is configured as a weight scale 101 that includes BLUETOOTH® connectivity to a networked device 810. The system of FIG. 8 may be used in a medical monitoring solution for persons who may require assistance with regular monitoring of a health parameter. For example, congestive heart failure (CHF) is being diagnosed with increasing frequency. An important factor in monitoring a patient with CHF is the amount of water that is being retained by the body. Increased water retention increases pressure to the heart and lungs and exacerbates the patient's condition. Water retention is typically monitored through measuring the patient's body weight. Accordingly, regular monitoring of body weight may provide indications as to when the body is retaining water and placing the patient at increased risk. Frequently, CHF patients include the elderly, who for a number of reasons may be non-compliant with a regimen of regularly scheduled weight measurements and logging and/or reporting of weight measurements.

In a system according to the invention, the patient may be provided with a weight scale having BLUETOOTH® capabilities 101. The weight scale 101 may be kept at the patient's home providing routine access to the device. A networked device 810 is provided and installed in the patient's home in the vicinity of the weight scale 101. The networked device 810 includes a BLUETOOTH® component 811, which is paired with the BLUETOOTH® component 211 of weight scale 101. The networked device 810 is further in communication with a local computer network (not shown). The networked device 810 may be connected to the local computer network through a wired connection such as USB or Ethernet or may be wirelessly connected through a communication protocol such as WiFi. The networked device 810 is further connected via the local network connection to a gateway, which provides network connectivity to an internetwork 820 to remote computing devices. For example, the networked device 810 may be connected to the Internet 820 through a router connected to service provided by an Internet Service Provider (ISP).

Each time the patient steps on the weight scale, the scale 101 is activated and wakes the BT communication component 211, which connects with the networked device 810 via BLUETOOTH®. The pressure sensors in the scale 101 sense the body weight of the patient and produce a numeric value of the sensed weight. The numeric value is validated by a processor of the weight scale and once validated, is provided to the BLUETOOTH® communication component 211 in the weight scale 101. The numeric value is transmitted via BLUETOOTH® in a HID format to the networked device 810. The networked device 810 receives the transmitted numeric value representative of the patient's weight and transmits it via the internetwork 820 to a remote computing device 830, 840.

The receiving remote computing device may be a computer connected to the internetwork 820. The remote computing device may be operated by a medical service provider, such as a healthcare provider 840 or a health monitoring company 830. Healthcare provider's remote computing device 840 may be connected to internetwork 820 by communications link 845. Communications link 845 may include networking connections as known in the art of computer networks. For example, remote computing device 840 may be connected to a local area network via a network adapter. The network adapter may be configured as a wired connection such as Ethernet, or may connect to the local area network via a wireless network connection such as WiFi. The local area network may be connected to a gateway provided by an Internet Service Provider (ISP), which provides data communications between the local area network (and remote computing device 840) and internetwork 820. The internetwork 820 further provides data communication between the local area network of remote computing device 840 and the patient's networked device 810. Remote Monitoring Service computing device 830 is connected to internetwork 820 via communications link 835, which operates similarly to communications link 845 described above.

The patient's weight measurement is received at the remote computing device 830, 840 and communicated to a software application configured to receive and save the patient's weight measurement. The receiving application does not need any special interface with the remote computing device 830, 840, the networked device 810 at the patient location, or the sensing device 101 (e.g. the weight scale). The weight measurement is provided via a BLUETOOTH® HID class definition and is provided to the networked device 810 via the HID port 812 in the networked device 810. The application at the networked device receives the weight measurement as an HID input and inserts the value into the selected field in the application running at the networked device 810. The input field may be selected manually, or the appropriate input field may have focus set to it automatically. For example, when a new weight measurement is received, the networked device 810 may be configured to be awakened, a software application started and an input field in the application selected, wherein the selected input field is the next unused field in the application. In one example, the application may be a database application, which creates a new input record including a data field for a patient's weight when the networked device 810 is awakened and inserts the received weight measurement into the associated data field of the new record. In this way, the patient is not burdened with logging weight measurements, or remembering weight measurements displayed at the weight scale 101. Thus, the patient's body weight may be measured and monitored over time remotely. Abnormal conditions, or conditions which increase the patient's risk of complications, may be identified by a trained observer, or automatically detected by software configured for analyzing the input data and identifying risks. Warnings or alerts may be provided to medical personnel so intervening action may be taken.

Those skilled in the art of computer programming will appreciate that the invention may be implemented in a system of computer units or processors communicatively coupled to one another over a network, such as a wide area network. "Processor", as used herein, refers generally to a processing device such as a microprocessor having a CPU. A CPU generally includes an arithmetic logic unit (ALU), which performs arithmetic and logical operations, and a control unit, which extracts instructions (e.g. code) from memory and decodes and executes them, calling on the ALU when necessary. "Memory", as used herein refers to one or more devices capable of storing data, such as in the form of chips, tapes, disks or drives. Memory may take the form of one or more random-access memory (RAM), read-only memory (ROM), programmable read-only memory (PROM), erasable programmable read-only memory (EPROM), or electrically erasable programmable read-only memory (EEPROM) chips by way of non-limiting example only. Memory may be internal or external to an integrated unit including a processor. Memory may be internal or external to an integrated unit including a personal computer or mobile device. Memory unit preferably stores a computer program, e.g. a sequence of instructions being executable by the processor.

While the foregoing invention has been described with reference to the above-described embodiment, various modifications and changes can be made without departing from the spirit of the invention. Accordingly, all such modifications and changes are considered to be within the scope of the appended claims. Accordingly, the specification and the drawings are to be regarded in an illustrative rather than a restrictive sense. The accompanying drawings that form a part hereof, show by way of illustration, and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

Such embodiments of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations of variations of various embodiments. Combinations of the above embodiments, and other embodiments not specifically described herein, will be apparent to those of skill in the art upon reviewing the above description.

The invention claimed is:

1. A system for remote monitoring of a parameter comprising:
    a sensing device comprising:
        at least one sensor configured to measure a property of at least one parameter;
        a sensing device processor to process the measured property and convert the measured property to a numeric value in Human Interface Device (HID) protocol with a system interrupt request having a high system priority; and
        a first wireless communications component configured to transmit the numeric value in HID protocol with the system interrupt request having the high system priority;
    a remote processing device comprising:
        a second wireless communication component in communication with the first wireless communications component of the sensing device; and
        a software adapter stored in a memory in the remote processing device, the software adapter configured to:
            receive, by the second wireless communication component from the first wireless communication component, a data stream including one or more parameters in HID compliant protocol with the system interrupt request having the high system priority;

parse the received data stream to identify each parameter value contained in the data stream;

responsive to identification of each parameter value contained in the data stream, select one parameter value in the received data stream for entry into a selected application on the remote processing device;

generate a message prompt directing a user to set focus on a data entry field of the selected application into which the selected parameter value is to be inserted; and input the selected parameter value to the data entry field in HID compliant protocol with the system interrupt request having the high system priority.

2. A system of claim 1, wherein the software adapter is further configured to:

determine whether the selected parameter value is a last parameter value in the received data stream;

responsive to a determination that the selected parameter value is the last parameter value, end processing by the software adapter;

responsive to a determination that the selected parameter value is not the last parameter value in the received data stream, select another parameter value for entry into the selected application on the remote processing device and repeat the message prompt generation and input of the selected another parameter value steps until the selected parameter value is the last parameter value.

3. The system of claim 1, wherein the sensing device comprises a weight scale and the at least one parameter comprises one of a body weight, a body mass index value, a body fat percentage, and a body water percentage.

4. The system of claim 1, wherein said at least one sensor includes at least one of:
a load cell;
an electrode;
a temperature sensor;
a pressure sensor;
an accelerometer;
an optical sensor;
a position sensor;
a displacement sensor; and
a force sensor.

5. The system of claim 1, wherein the sensing device processor is configured to send a signal to the first wireless communications component, wherein the sent signal is configured to power off the first wireless communications component at a time when the at least one sensor is measuring the property of the at least one parameter and the sent signal is configured to power on the first wireless communications component at a time when the sensing device processor is sending the processed information to the first wireless communications component.

6. The system of claim 1, wherein said first wireless communications component and said second wireless communications component comprise a short range wireless communications component configured to communicate according to a BLUETOOTH protocol.

7. The system of claim 6, wherein said remote processing device comprises one of a smart phone, a fitness tracking device, a computer, and a tablet computing device.

8. A method for remote monitoring of a parameter comprising:

receiving, by a second wireless communication component of a remote processing device from a first wireless communication component of a sensing device, a data stream including one or more parameter values in HID compliant protocol with the system interrupt request having the high system priority;

parsing, by a software adapter stored in a memory of the remote processing device, the received data stream to identify each parameter value contained in the data stream;

responsive to identification of each parameter value contained in the data stream, selecting one parameter value in the received data stream for entry into a selected application on the remote processing device;

generating a message prompt directing a user to set focus on a data entry field of the selected application into which the selected parameter value is to be inserted; and inputting the selected parameter value to the data entry field in HID compliant protocol with the system interrupt request having the high system priority.

9. The method of claim 8, further comprising:

determining, by the software adapter, whether the selected parameter value is a last parameter value in the received data stream in the received data stream;

responsive to a determination that the selected parameter value is the last parameter value, ending processing by the software adapter;

responsive to a determination that the selected parameter value is not the last parameter value in the received data stream, selecting, by the software adapter, another selected parameter value for entry into the selected application on the remote processing device and repeating the message prompt generation and inputting of the another selected parameter value steps until the selected parameter value is the last parameter.

10. The method of claim 8, wherein the sensing device comprises a weight scale and the at least one parameter comprises one of a body weight, a body mass index value, a body fat percentage, and a body water percentage.

11. The method of claim 8, wherein the sensing device comprises at least one sensor, wherein the at least one sensor includes at least one of:
a load cell;
an electrode;
a temperature sensor;
a pressure sensor;
an accelerometer;
an optical sensor;
a position sensor;
a displacement sensor; and
a force sensor.

12. The method of claim 8, wherein the data stream is received by the second wireless communications component from the first wireless communications component according to a BLUETOOTH protocol.

13. The method of claim 8, further performing, by the software adapter, at least one validation procedure on the parameter value.

14. The method of claim 8, further comprising sending, by the sensing device processor, a signal to the first wireless communications component, wherein the sent signal is configured for powering off the first wireless communications component at a time when the at least one sensor is measuring the property of the at least one parameter and the sent signal is configured for powering on the first wireless communications component at a time when the sensing device processor is sending the processed information to the first wireless communications component.

15. A sensing device configured for measuring at least one parameter comprising:
- at least one sensor configured to measure a property of the at least one parameter;
- a memory;
- a sensing device processor in communication with the at least one sensor and the memory;
- a first communications component in communication with the sensing device processor;
- wherein the memory has stored therein, computer instructions that when executed by the sensing device processor:
  - pair the sensing device with a remote processing device;
  - responsive to setting focus on a data entry field of an application of the remote processing device into which a selected parameter is to be inserted, activate the at least one sensor to measure a property of a parameter;
  - convert the measured property to a numeric value in Human Interface Device (HID) protocol with a system interrupt request having a high system priority;
  - transmit, by the first communications component, the numeric value in HID protocol with the system interrupt request having the high system priority to a second communications component of the remote processing device; and
- wherein the remote processing device is configured to receive, by the second communications component, the numeric value in HID compliant protocol with the system interrupt request having the high system priority and input the numeric value into the data entry field of the selected application on the remote processing device.

16. The sensing device of claim 15, wherein the memory stores further computer instructions that when executed by the sensing device processor, repeat, for one or more additional properties, the steps of activating a corresponding sensor to measure the one or more additional properties, converting the measured property, and transmitting the corresponding numerical value to the second communications component of the remote processing device;
- wherein the remote processing device is configured to receive, by the second communications component, the corresponding numerical value in HID compliant protocol with the system interrupt request having the high system priority and input the numeric value into the data entry field of the selected application on the remote processing device.

17. The sensing device of claim 15, further comprising a pairing button, wherein the computer instructions when executed by the sensing device processor pair the sensing device with the remote processing device responsive to actuation of the pairing button.

18. The sensing device of claim 15, wherein the computer instructions when executed by the sensing device processor are configured to automatically pair the sensing device with the remote processing device when the sensing device and the remote processing device have been previously paired and the remote processing device is within a pairing range of the sensing device.

19. The sensing device of claim 15, wherein the computer instructions when executed by the sensing device processor are configured to pair the sensing device with the remote processing device according to a BLUETOOTH protocol.

20. The sensing device of claim 15, wherein the sensing device comprises a weight scale and the at least one parameter comprises one of a body weight, a body mass index value, a body fat percentage, and a body water percentage.

* * * * *

UNITED STATES PATENT AND TRADEMARK OFFICE
CERTIFICATE OF CORRECTION

PATENT NO. : 10,820,828 B2  
APPLICATION NO. : 16/265445  
DATED : November 3, 2020  
INVENTOR(S) : Steven Petrucelli and Jack Ko Page 1 of 1

It is certified that error appears in the above-identified patent and that said Letters Patent is hereby corrected as shown below:

In the Claims

Claim 9, Column 20, Line 25, delete the second occurrence of the phrase "in the received data stream."

Signed and Sealed this  
Thirtieth Day of March, 2021

Drew Hirshfeld  
*Performing the Functions and Duties of the*  
*Under Secretary of Commerce for Intellectual Property and*  
*Director of the United States Patent and Trademark Office*